United States Patent [19]
Olah

[11] Patent Number: 5,110,778
[45] Date of Patent: May 5, 1992

[54] BORON ALUMINUM AND GALLIUM PERFLUORO ALKANESULFONATE AND RESINSULFONATE CATALYSTS

[76] Inventor: George A. Olah, 2252 Gloaming Way, Beverly Hills, Calif. 90210

[21] Appl. No.: 111,546

[22] Filed: Oct. 23, 1987

Related U.S. Application Data

[62] Division of Ser. No. 920,329, Oct. 17, 1986, Pat. No. 4,721,559.

[51] Int. Cl.$^5$ .............................................. B01J 31/02
[52] U.S. Cl. ..................................... 502/168; 502/171; 502/202; 585/458; 585/474; 585/730; 585/747; 585/749; 562/110
[58] Field of Search ........................ 502/168, 171, 202; 260/513 F; 585/458, 474, 730, 747, 749

[56] References Cited

U.S. PATENT DOCUMENTS

| | | | |
|---|---|---|---|
| 3,282,875 | 11/1966 | Conolly et al. | 260/29.6 |
| 3,852,184 | 12/1974 | Siskin et al. | 208/64 |
| 3,882,093 | 5/1975 | Cavanaugh et al. | 260/79.3 MU |
| 4,035,286 | 7/1977 | McCaulay et al. | 208/134 |
| 4,041,090 | 8/1977 | McClure | 260/671 R |
| 4,472,268 | 9/1984 | Olah | 208/134 |
| 4,508,618 | 4/1985 | Olah | 208/134 |
| 4,547,474 | 10/1985 | Olah | 502/168 |

FOREIGN PATENT DOCUMENTS 0171893  2/1986  European Pat. Off. .

OTHER PUBLICATIONS

Olah et al., "Superacids", John Wiley & Sons, New York (1985), pp. 10-11 and 33-52.
Pine, "Organic Chemistry", McGraw-Hill Book Company, 5th Ed. (1988), pp. 650-656.
Meyers et al., "Stereoselectivity in the Aldol Reaction. The Use of Chiral and Achiral Oxazolines as Their Boron Azaenolates", Tetrahedron, 40(12), pp. 2309-2315, Chem. Abstract No. CA101(25):229969z.
Abdel-Magid et al., "Metal-Assisted Aldol Condensation of Chiral α-Halogenated Imide Enolates: A Stereo Controlled Chiral Epoxide Synthesis", J. Am. Chem. Soc., 108(15), pp. 4595-4602, Chem. Abstract No. CA105(15):133672d.
Collomb et al., "Cationic Polymerization and Electrophilic Reactions Promoted by Metal Salts of Strong Acids", Cationic Polym. Relat. Processes, Proc. Int. Symp., pp. 49-67, 1983, Chem. Abstract No. CA101(22):192533z.
Collomb et al., "Cationic Polymerization Induced by Metal Salts of Strong Acids: Kinetics and Mechanisms", Proc. Ivpac, Macromol. Symp., p. 136, 1982, Chem. Abstract No. CA99(16):123000b.
Olah et al., J. Org. Chem. 49, 4591-4594 (1984).
Collomb et al., Europ. Polym. J., 16, pp. 1135-1144 (1980).
Collomb et al., Makromol. Chem., Rapid Commun., 1, 489-491 (1980).
Engelbrecht, Von A. und Tschager, E., Z. anorg. allg. Chem., 433, pp. 19-25 (1977).
Olah et al., J. Org. Chem. 49, 4591-4594 (1984).

*Primary Examiner*—William R. Dixon, Jr.
*Assistant Examiner*—Anthony J. Green
*Attorney, Agent, or Firm*—Pennie & Edmonds

[57] ABSTRACT

Boron, aluminum and gallium $C_1$–$C_{18}$ perfluoroalkanesulfonates $(CF_3(CF_2)_nSO_3)_3M$ (M = B, Al, Ga; n = 0–17) as well as perfluororesin sulfonates such as Nafionates are new, highly effective Friedel-Crafts catalysts. In contrast to volatile aluminum and boron trihalides, the Group III-B perfluoroalkanesulfonates are generally of low or no volatility and, except for boron triflate and some of its homologs, only sparingly soluble incommon organic solvents. This allows their use as solid or supported Friedel-Crafts catalysts of wide utility and scope in continuous heterogenous catalytic processes. At the same time, boron triflate and related lower perfluoroalkanesulfonates are particularly efficient soluble catalysts in solution reactions.

5 Claims, No Drawings

BORON ALUMINUM AND GALLIUM PERFLUORO ALKANESULFONATE AND RESINSULFONATE CATALYSTS

This is a division of application Ser. No. 920,329, filed Oct. 17, 1986, now U.S. Pat. No. 4,721,559.

TECHNICAL FIELD

The present invention relates to a new class of boron, aluminum and gallium perfluoro alkanesulfonate or resinsulfonate Friedel-Crafts catalysts.

BACKGROUND OF THE INVENTION

In the course of more than 100 years of Friedel-Crafts chemistry, two catalysts achieved preeminence. Anhydrous aluminum trichloride was introduced by Friedel and Crafts themselves and maintained its wide use despite some of its unfavorable properties, i.e. it is a subliming solid with only limited solubility in apolar or hydrocarbon solvents. Boron trifluoride became a significant catalyst since the 1930's based on fundamental studies by Meerwein and others. As it is a low boiling gas (bp. $-100°$ C.), some of its more convenient complexes are frequently used, albeit reduced in reactivity, such as the ether complex. Although a significant number of other Lewis acid halide (and pseudo halide) catalysts are also applied on occasion, none of them achieved similar wide application. Since the 1960's, superacidic catalysts based on antimony pentafluoride gained significance. Friedel-Crafts catalysts are well reviewed (see G. A. Olah, "Friedel-Crafts Chemistry", Wiley Interscience, New York, 1973; G. A. Olah, G. K. S. Prakash and J. Sommer, "Superacids", Wiley-Interscience, New York, 1986).

All the active Friedel-Crafts catalysts, such as the reactive halides of boron, aluminum, and gallium, are substantially volatile or sublime and consequently can not be used as solid or supported catalysts in heterogenous gas phase processes. This is a serious shortcoming of Friedel-Crafts chemistry forcing it to be usually operated in closed, batchwise reactors. In contrast, the plurality of modern chemical and petrochemical processes increasingly use heterogenous catalytic gas phase technology. My invention now discloses a new class of highly efficient Friedel-Crafts catalysts which can also overcome this limitation.

SUMMARY OF THE INVENTION

The invention relates to new, highly efficient Friedel-Crafts type catalysts. In one embodiment, these catalysts comprise a Group III-B metal perfluoro alkanesulfonate. Also, perfluoro resin sulfonates may be used instead of perfluoro alkane sulfonates with similar results. The preferred group III-B metals include boron, aluminum and gallium, and the carbon chain of the alkane group can range from 1 to 18 carbon atoms. These catalysts can be used alone or can be deposited on a suitable support.

The invention also relates to a process for effecting hydrocarbon transformations which comprises contacting a $C_4$ to $C_{30}$ hydrocarbon with these catalysts. Continuous heterogeneous flow conditions are preferred for effecting these transformations, which include alkylation, isomerization, catalytic cracking, polymerization, halogenation, acylation, formylation, sulfonylation or nitration.

DETAILED DESCRIPTION OF THE PREFERRED EMBODIMENTS

I have discovered that a group III-B metal (i.e. boron, aluminum or gallium) perfluoroalkanesulfonate, such as the tris-trifluoromethanesulfonates (triflates) or higher homologous perfluoroalkanesulfonates are convenient and effective new Friedel-Crafts catalysts for use in continuous flow heterogeneous hydrocarbon conversion processes. Due to its monomeric nature, good solubility and favorable physical properties and high reactivity, boron triflate $(CF_3SO_3)_3B$ is the preferred catalyst of wide utility and general use in solution chemistry. Aluminum $(CF_3SO_3)_3Al$ and gallium triflates $(CF_3SO_3)_3Ga$, on the other hand, are highly associated, high melting compounds with low solubility. This renders their activity in solution chemistry somewhat limited, necessitating heterogeneous conditions, but they find excellent utility as solid or supported heterogeneous catalysts for gas phase reactions.

Boron triflate was first prepared by Engelbrecht and Tshager in trifluoromethanesulfonic (triflic) acid solution as its conjugate Bronsted-Lewis superacid, $2CF_3SO_3H\text{-}B(OSO_2CF_3)_3$. (Z. Anorg. Allgem. Chem. 1977, 19, 433). Olah, Laali and Farooq explored the catalytic activity of this conjugate superacid (J. Org. Chem. 1983, 49, 4591). They also obtained boron triflate free of protic acids, but it was not further characterized nor was its catalytic activity studied. Collomb, Gandini and Cheradome (Macromol. Chem. Rapid Comm. 1980, 1, 489; Europ. Polym. Journ., 1980 16, 1135) reported the polymerization of some alkenyl monomers with metal perchlorates and triflates, which included aluminum and gallium triflate. They assumed an ionic dissociation according to:

with $AlTf_2^+$ initiating the polymerization of olefins by:

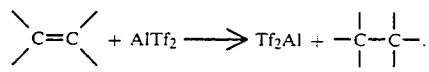

No substantiation for the suggested claims was provided and no similar dissociation equilibrium is known even for aluminum halides. No teaching for the use of Group III-B metal triflate catalysts in Friedel-Crafts chemistry was made, nor were most of the higher homolog perfluoroalkanesulfonates or polymeric perfluoroalkane sulfonates previously made and their catalytic use was never reported.

Boron triflate is conveniently prepared by reacting boron trichloride, boron tribromide or phenyldichloroborane with triflic acid. The reaction must be carried out by adding the triflic acid to the boron halides and removing in vacuum the hydrogen halides formed:

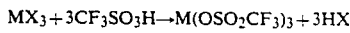

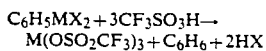

M = B, Al, Ga

Aluminum and gallium triflates can be similarly prepared, including phenylaluminum (or phenyl gallium) sesquihalides.

The physical properties of boron triflate, which is a low melting (43° C.), relatively volatile solid, are very different from those of aluminum and gallium triflates which are high melting point, powdery solids (mp. >350° C.). Boron triflate is extremely hygroscopic and well soluble in many solvents including such as methylene chloride, 1,1,2-trichlorotrifluoromethane (Freon-13), $SO_2$, $SO_2ClF$, nitromethane, etc. Aluminum and gallium triflates, in contrast are not soluble in most of these solvents and show only very limited solubility in $SO_2$, $SO_2ClF$ and nitromethane. Both aluminum and gallium triflate, however, are soluble in highly coordinating solvents such as acetonitrile.

Higher perfluoroalkanesulfonates of 2 to 18 carbon atoms such as perfluorobutyl, -hexyl, -octyl, -decyl, -dodecyl and -octadecyl sulfonates are similarly prepared from the corresponding sulfonic acids.

$$3CF_3(CF_2)_nSO_3H + MX_3 \rightarrow ((CF_3CCF_2)_nSO_3)_3M + 3MX$$

M = B, Al, Ga,
X = Cl, Br,
n = 1-17

They show decreasing solubility with increasing molecular weight in accordance with behavior of their single carbon triflate analogs.

The catalysts of the invention can be used in solution, in a dispersion of solvents, or as solid or supported catalysts under conditions customary in homogeneous and heterogeneous catalysis.

Perfluorinated resinsulfonic acids also can be reacted with Group III-B metal halides (preferably chlorides or bromides) to obtain the corresponding metal resin sulfonates.

Perfluoroalkanesulfonic acid polymers were first developed by the DuPont Company. They are copolymers of perfluorovinyl ethers and perfluorovinyl sulfonic acids. The acidic form of the resin, Nafion-H, is a widely used solid superacid catalyst in synthesis (for a review, see G. A. Olah, P. S. Iyer and G. K. S. Prakash, "Synthesis", 1986, 513-531).

This catalyst comprises a perfluorinated polymer having sulfonic acid groups in the amount of about 0.01 to 5 mequiv/gram catalyst. The polymer catalyst contains a repeating structure which can be depicted as:

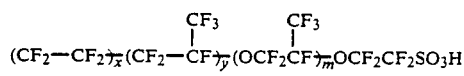

or

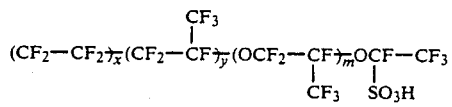

where the ratio of x over y varies from about 2 to about 50, and m is 1 or 2. Polymer sulfonic acids of the above structure can be prepared in various ways. One method, disclosed in Conolly et. al., U.S. Pat. No. 3,282,875 and Cavanaugh et. al., U.S. Pat. No. 3,882,093, comprises polymerizing the corresponding perfluorinated vinyl compounds. It is also possible to prepare polymer catalyst according to U.S. Pat. No. 4,041,090 by copolymerizing the corresponding perfluorinated vinyl ethers with perfluoroethylene and/or perfluoro-alpha-olefins.

Group III-B metal Nafionates are prepared by reacting the free sulfonic acid resin (Nafion-H) with the corresponding metal chloride (bromides) and recovering the hydrogen halides formed in vacuum.

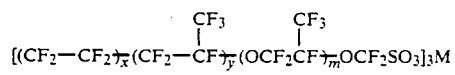

or

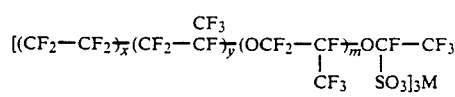

M = B, Al, Ga

It is also possible that certain Group III-B metal sites contain only one or two attached Nafionates and are thus mixed halide Nafionates of the type $Naf\,MX_2$ or $Naf_2MX$ X = Cl, Br although at the clustering sites, metal tris-Nafionates are probable.

Other perfluorinated polymer sulfonic acids capable of giving catalytically active Group III-B metal salts include resinsulfonic acids analogous to Nafion, such as polytrifluoroethylenesulfonic acids and tetrafluoroethylene-trifluoroethylenesulfonic acid polymers.

The catalyst of the invention may be absorbed on a suitable support material. Alumina, silica or mixtures thereof as well as other chalcides can be used for this purpose.

All metal perfluoroalkanesulfonate catalysts were characterized through their nuclear magnetic resonance including $^{11}B$, $^{13}C$, $^{19}F$, $^{27}Al$ and Ga and infrared spectroscopic spectra.

The catalytic activity of Group III-B perfluoroalkanesulfonates is illustrated by, but not limited to, such typical Friedel-Crafts reactions as alkylation, acylation, isomerization, cracking, polymerization, halogenation and the like. It is considered that all reaction types summarized and discussed in my monographs "Friedel-Crafts and Related Reactions", Vols. I-IV, Wiley-Interscience, New York, 1963-64, and "Friedel-Crafts Chemistry", Wiley-Interscience, New York, 1973, are advantageously catalyzed by the disclosed new catalyst of my present invention. Thus, the disclosures of these documents are expressly incorporated herein by reference.

Alkylation and isomerization, as well as de- and transalkylations, disproportionation, polymerization, cracking and related processes of hydrocarbons, are readily catalyzed by the catalysts of the present invention as described herein above. These processes are effected by contacting a charge of a hydrocarbon, or hydrocarbon mixture with the above described catalysts under the conventional conditions of the desired hydrocarbon conversion. Contacting of the catalyst with the hydrocarbon charge is facilitated by using such conventional systems as fixed bed systems, moving bed systems, fluidized bed systems, continuous or batch-type operations. The hydrocarbon conversions utilizing the presently described catalysts can be carried out either in the vapor phase, in the liquid phase, or as mixed phase operations. Conversions can also be carried out in the presence of hydrogen, or catalysts generally also cause concurrent cleavage reactions (cracking).

Alkylations can be particularly effectively carried out employing the catalysts of the present invention.

Aromatic and aliphatic hydrocarbons such as benzene, toluene, alkylbenzenes, naphthalene and the like, or straight chain or branched alkanes including methane, ethane, propane, butanes, pentanes, hexanes, etc., cycloalkanes and polycyclic alkanes, including adamantane and diamantane, as well as alkenes and alkynes are effectively alkylated by alkyl halides, olefins or other alkylating agents both in solution chemistry and in the gas phase reactions catalyzed by Group III-B metal perfluorosulfonate catalysts of my invention.

Alkylation of alkylatable hydrocarbons such as alkanes or aromatics with olefins, alkyl halides, alcohols, and other alkylating agents can be effected in the presence of the catalyst at temperatures between about 0° to about 200° C. and the pressure between about atmospheric and 50 atmospheres.

The catalysts of the present invention are also suitable for catalytic cracking of hydrocarbons. The hydrocarbon charge may comprise normal alkanes or complex mixtures of alkanes, naphthenes, and aromatics, such as they occur in petroleum, which is the feed normally used in commercial catalytic cracking units. Hydrocarbon cracking utilizing catalysts of the present invention can be conducted at temperatures ranging between 50° and 250° C. and pressures from atmospheric to 50 atmospheres or higher. Presence of hydrogen (hydrocracking) can be applied to further prolong catalyst life and, thus, cause more efficient cracking operations. In the use of the catalysts of the present invention for hydrocarbon conversion reactions hydrogen gas or naphthenic hydrocarbons can be used as moderators, which tend to decrease any concurrent cracking reactions. Operation in the presence of hydrogen and related hydrocarbon moderators are also particularly advantageous for isomerizations.

Isomerization of isomerizable $C_4$ to $C_{30}$ hydrocarbons, such as alkanes, naphthenes or alkyl-aromatic hydrocarbons may be effectively carried out utilizing the catalyst of this invention. Isomerization of straight-chain or slightly branched-chain alkanes containing 4 or more carbon atoms in their molecules, such as n-butane, n-pentane, n-hexane, n-heptane, n-octane, and the like, may be readily effected. Likewise, cycloalkanes containing at least 5 carbon atoms in the ring, such as alkyl cyclopentanes and cyclohexanes are effectively isomerized. These isomerizations are particularly suitable to produce high octane number branched alkane mixtures of the gasoline range. As examples of commercial mixtures, straight-run type or light naphtha fractions from conventional refinery operations can be mentioned. Isomerization of alkylbenzenes include those of xylenes, diethylbenzenes, cymenes, and other di- and poly-alkylbenzenes.

In carrying out isomerizations of isomerizible $C_4$ to $C_{20}$ hydrocarbons, contact between the catalyst and hydrocarbon charge is conducted at temperatures between about 0° and 300° C., preferably between 25° and 200° C., at pressures between atmospheric and 50 atmospheres or more. The hydrocarbon is passed over the catalyst as a gas or liquid generally admixed with hydrogen, with a liquid hourly space velocity generally between about 0.5 and 5.0 or a gaseous hourly space velocity between 50 and 5000. The resulting product is withdrawn from the reactor, and is separated by any suitable means such as fractional distillation. Any unreacted starting material may be recycled. The effective hydrocracking catalysts, based on this invention are not effected by the presence of sulfur and other impurities, and which normally cause rapid deactivation of conventional cracking catalysts. In view of the need of increased utilization of "heavy" petroleums and lower grade crudes, the new catalysts and process of this invention are of considerable commercial significance.

Catalysts of the invention are also effective for ring opening polymerizations such as of tetrahydrofuran and alkene oxides and other polymers adaptable for cationic polymerizations.

Friedel-Crafts acylations of aromatic and aliphatic hydrocarbons including formylation, acetylation, propionylation, benzoylation and the like are also catalyzed by the disclosed catalysts.

Aromatic and aliphatic hydrocarbons are also nitrated with nitryl chloride or nitrogen oxides and sulfonylated with alkyl or arylsulfyl halides in the presence of the Group III-B perfluoroalkanesulfonate catalysts. The nitration and acylation reactions can be carried out under the same conditions as for the isomerization reactions described above.

Catalytic halogenation (chlorination, bromination or iodination) of aromatic and aliphatic hydrocarbons takes places with ease and high selectivity. Noteworthy is the chlorination and bromination of methane which can be effected in solution or in the gas phase over aluminum triflate, supported boron triflate or related catalysts at temperatures between 20° to 250° C. giving selectively monohalogenation characteristic of electrophilic reactions as contrasted with non-selective radical reactions.

Other applications of the catalysts of present invention towards additional conversions of hydrocarbons should be apparent to those skilled in the art of hydrocarbon chemistry.

EXAMPLES

The scope of the invention is further described in connection with the following examples, which are set forth for the purpose of illustration and are not to be considered to limit the scope of the invention in any manner.

EXAMPLE 1

Aluminum tris-triflate $(CF_3SO_3)_3Al$ is prepared by placing a premeasured amount of anhydrous aluminum trichloride (tribromide) in a well dried three necked flask equipped with a magnetic stirrer, a pressure equalizing dropping funnel and dry nitrogen inlet. The flask is cooled and 3 equivalents of triflic acid are slowly added from the dropping funnel with efficient stirring whereby HCl (HBr) slowly evolves. The temperature was slowly raised until completion of the reaction. The flask is then evacuated in vacuum to remove any HX and residual triflic acid giving aluminum triflate as a slightly off colored solid.

EXAMPLE 2

$(C_4F_9SO_3)_3Al$ and $(C_{10}F_{21}SO_3)_3Al$ were prepared from the corresponding perfluoroalkanesulfonic acids as in Example 1.

EXAMPLE 3

To boron tribromide (1 equivalent) placed in a three necked flask was slowly added 3 equivalents of triflic acid and preparation carried out as in Example 1 giving boron tris-triflate $(CF_3SO_3)_3B$ as a colorless low melting solid (mp 43° C.).

EXAMPLE 4

To gallium trichloride (1 equivalent) was added 3 equivalents of triflic acid and preparation carried out as in Example 1 to give gallium tris-triflate $(CF_3SO_3)_3Ga$.

EXAMPLE 5

Benzene (5 equivalents) was reacted in a batchwise stirred alkylation apparatus protected from moisture in the presence of 0.2 equivalents of boron triflate catalyst with 1.5 equivalents ethylene gas. The temperature was controlled as to keep it at about 50° C. Work-up gave 1.2 equivalents of ethylbenzene with diethylbenzenes and some higher alkylates amounting to 0.3 equivalents.

EXAMPLE 6

Aluminum triflate was placed in the reaction tube of a heterogeneous gas phase alkylation reactor and a mixture of 2 equivalents of benzene and 1 equivalent of ethylene was continuously passed through the catalyst at a temperature of about 150° C. with a gas liquid hourly space velocity (ml/g-hr) of 250. The alkylation product contained an average of 0.6 equivalents of ethylbenzene and 0.13 equivalents of dialkylbenzenes.

EXAMPLE 7

A 2:1 equivalent mixture of benzene and propylene was passed over a catalyst comprised of 5% boron triflate supported on charcoal in a continuous tube reactor at a temperature of 145° C. and GHSV of 250. Product composition was 0.47 equivalents of cumene and smaller amounts of diisopropyl benzenes.

EXAMPLE 8

0.015 equivalents of boron triflate dissolved in methylene chloride was reacted with 1 equivalent of toluene and 0.5 equivalents of 1-chloroadamantane at 30° C. for 15 minutes. Upon usual work-up, 0.38 equivalents of methyl adamantylbenzenes were obtained composed of about 54% of meta isomer, 37% of para, and 9% ortho isomer.

EXAMPLE 9

1 equivalent of normal butane was reacted in a pressure autoclave in the presence of 0.1 equivalents of boron triflate dissolved in Freon 113 (1,1,2-trichlorotrifluoroethane) at 50° C. for 1 hour. Gas liquid chromatographic analysis of the products showed formation of 0.4 equivalents of isobutane with small amounts of propane and pentanes.

EXAMPLE 10

Reaction was carried out as in Example 8, but with boron tris perfluorobutanesulfonate as catalyst. 0.27 equivalents of isobutane was obtained.

EXAMPLE 11

1 equivalent of a mixture of exo- and endo-trimethylenenorbornane (tetrahydrodicyclopentadiene) was reacted with 0.2 equivalents of boron tris-triflate catalyst in Freon 113 solution at room temperature for 12 hours. A nearly quantitative yield of 0.98 equivalents of adamantane was obtained with no byproducts.

EXAMPLE 12

A 2:1 molar equivalent mixture of methane and chlorine was passed over a 5% aluminum triflate supported on charcoal catalyst at 150° C. in a catalytic tube reactor. The product obtained contained 97% methyl chloride and 3% methylene chloride with a 38% chlorine conversion.

EXAMPLE 13

Previously dried and distilled tetrahydrofurane (THF) was stirred in a reaction flask protected from moisture and air with 0.02 equivalents of aluminum tris-triflate. After an initiation period of about 1 hour, polymerization takes place giving an increasingly viscous reaction mixture. Portions of additional THF can be now added till a total of 5 equivalents were polymerized. Work-up gave a transparent polymethylene ether polymer. Molecular weight reached $1.5 \times 10^6$.

EXAMPLE 14

Benzene (1 equivalent) was reacted with acetyl chloride (0.5 equivalents) in the presence of 0.25 equivalents of gallium triflate catalyst at 50°-60° C. for 1 hour giving 0.35 equivalents of acetophenone.

While it is apparent that the invention herein disclosed is well calculated to fulfill the desired results, it will be appreciated that numerous modifications and embodiments may be devised by those skilled in the art, and it is intended that the appended claims cover all such modifications and embodiments as fall within the true spirit and scope of the present invention.

What is claimed is:

1. A Friedel-Crafts catalyst comprising a Group III-B metal salt of one of a perfluorinated polymeric resinsulfonic acid, a polytrifluoroethylene-sulfonic acid, or a tetrafluoroethylene-trifluoroethylene-sulfonic acid copolymer.

2. The catalyst of claim 1 wherein the Group III-B metal is boron, aluminum, or gallium.

3. The catalyst of claim 1 further comprising a suitable support.

4. A Friedel-Crafts catalyst consisting essentially of a gallium perfluorinated polymeric resin sulfonic acid, polytrifluoro ethylene-sulfonic acid, or tetrafluoroethylene-trifluoroethylene-sulfonic acid copolymer.

5. The catalyst of claim 4 further including a suitable support.

* * * * *